United States Patent
Lee et al.

(10) Patent No.: US 9,714,883 B2
(45) Date of Patent: Jul. 25, 2017

(54) BEARING TEST APPARATUS FOR TESTING DURABILITY OF BEARING

(71) Applicant: KOREA INSTITUTE OF SCIENCE AND TECHNOLOGY, Seoul (KR)

(72) Inventors: Yong Bok Lee, Seoul (KR); Bokseong Choe, Gunpo-si (KR); Jeon Kook Lee, Seongnam-si (KR); Sol-Ji Ryu, Ansan-si (KR); Byoungkuk Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 356 days.

(21) Appl. No.: 14/506,121

(22) Filed: Oct. 3, 2014

(65) Prior Publication Data

US 2016/0025592 A1 Jan. 28, 2016

(30) Foreign Application Priority Data

Jul. 23, 2014 (KR) .................. 10-2014-0093115

(51) Int. Cl.
*G01M 13/04* (2006.01)
*G01L 5/00* (2006.01)
(Continued)

(52) U.S. Cl.
CPC .......... *G01M 13/04* (2013.01); *G01L 5/0009* (2013.01); *G01N 29/045* (2013.01); *G01N 29/14* (2013.01);
(Continued)

(58) Field of Classification Search
CPC ...... G01N 29/045; G01N 29/14; G01N 29/46; G01N 2291/2696; G01M 13/04; G01M 13/045; G01L 5/0009
See application file for complete search history.

(56) References Cited

U.S. PATENT DOCUMENTS 3,685,342 A * 8/1972 Gordon ................ G01M 13/04
73/9
4,196,635 A 4/1980 Zuber et al.
(Continued)

FOREIGN PATENT DOCUMENTS

KR 10-2004-0033827 A 4/2004
KR 10-0724799 B1 6/2007
(Continued)

OTHER PUBLICATIONS

"History of Space Shuttle Main Engine Turbopump Bearing Testing", by Gibson et al., Materials and Processes Lab, Mechanical Test Branch, Tribology Team, JANNAF conference, May 2010.*
(Continued)

*Primary Examiner* — Paul West
*Assistant Examiner* — Xin Zhong
(74) *Attorney, Agent, or Firm* — NSIP Law

(57) ABSTRACT

A bearing test apparatus has a bearing cap coupled to an outer ring of a bearing to be tested (a "test bearing"), a driving rotary shaft coupled to an inner ring of the test bearing to rotate the inner ring, and a bearing torque meter for measuring a single torque of the test bearing, wherein an extension bar is formed at the bearing cap to protrude thereon, wherein the bearing torque meter includes a measurement rod configured to contact the extension bar and be fixed to support the extension bar in a direction opposite to a rotating direction of the driving rotary shaft, and a power sensor for measuring a force applied to the measurement rod, wherein the single torque of the test bearing is calculated based on a distance from the driving rotary shaft to the measurement rod and a force applied to the measurement rod.

15 Claims, 4 Drawing Sheets

(51) Int. Cl.
*G01N 29/04* (2006.01)
*G01N 29/14* (2006.01)
*G01N 29/46* (2006.01)

(52) U.S. Cl.
CPC ..... *G01N 29/46* (2013.01); *G01N 2291/2696* (2013.01)

(56) References Cited

U.S. PATENT DOCUMENTS

| | | | |
|---|---|---|---|
| 4,763,508 A | | 8/1988 | Buck |
| 5,311,763 A | * | 5/1994 | Gibbs, Jr. ............... G01N 19/02 73/9 |
| 5,959,189 A | * | 9/1999 | Jeng ....................... G01M 13/04 73/10 |
| 6,009,764 A | * | 1/2000 | Fukunaga ............. G01L 5/0009 384/448 |
| 2005/0041898 A1 | * | 2/2005 | Yamada .................. F16C 19/52 384/490 |
| 2008/0234964 A1 | | 9/2008 | Miyasaka et al. |
| 2013/0342685 A1 | * | 12/2013 | Mochiki ................ G01N 23/05 348/135 |

FOREIGN PATENT DOCUMENTS

| | | |
|---|---|---|
| KR | 10-0949242 B1 | 3/2010 |
| KR | 10-1221554 B1 | 1/2013 |
| WO | WO 2006/030786 A1 | 3/2006 |

OTHER PUBLICATIONS

Lee, Yong Bok, et al. "Evaluation of Turbopump cryogenic ball bearing operation durability for Space launch vehicle (75-ton class)" Journal of Korean Society of Mechanical Engineers, 2013, (3 pages, in Korean, with English language abstract translation).

Jeon, Seong Min, et al. *Evaluation of Friction Torque for a Turbopump Ball Bearing,* Journal of the KSTLE vol. 27, No. 1, Feb. 2011, pp. 25-33.

Jo, Ju Hyeon, et al. *Development of Cryogenic Test Rig for Ball-Bearing and Evaluation of the Performance of the Prototype Ball-Bearing of Turbo pump.* Journal of the KSTLE vol. 28, No. 4, Aug. 2012, pp. 167-172.

* cited by examiner

BEARING TEST APPARATUS FOR TESTING DURABILITY OF BEARING

CROSS-REFERENCE TO RELATED APPLICATION

This application claims priority to Korean Patent Application No. 10-2014-0093115, filed on Jul. 23, 2014, and all the benefits accruing therefrom under 35 U.S.C. §119, the contents of which in its entirety are herein incorporated by reference.

BACKGROUND

Field

The present disclosure relates to a bearing test apparatus, and more particularly, to a test apparatus for testing durability of a bearing.

Description About National Research and Development Support

This study was supported by the Development of Core Space Technology Project of Ministry of Science, ICT and Future Planning, Republic of Korea (Project No. 1711005864) under the superintendence of National Research Foundation of Korea.

Description of the Related Art

A bearing is a mechanical element for fixing a shaft of a rotating machine to a position and protecting the rotation of the shaft while supporting the weight of the shaft and a load applied to the shaft.

This industrial bearing serves as an important component in machinery of every equipment or installation associated with fabrication and production lines in the overall industries.

In order to ensure excellent dynamic stability and reduce oscillation or vibration, the durability of the bearing should be ensured first, and the durability and stability of a designed and fabricated bearing should be evaluated.

One of main factors associated with service life of a bearing is a bearing torque which should be endured by the bearing in operation. In a related art, however, an effective method for directly measuring a single torque of a bearing has not been proposed.

In addition, a general industrial bearing is mostly operated in a grease-lubricating or oil-lubricating state, and the durability is also evaluated under conditions similar to an actual use environment.

However, a so-called "cryogenic bearing" operating in a cryogenic environment such as a LNG pump or a cryogenic turbo pump is used as an important part. The cryogenic bearing is spotlighted in a space industry field or the like.

However, an existing bearing durability evaluating device or method cannot be directly applied to a cryogenic bearing, and a cryogenic bearing evaluating technique and method is not yet systematically established.

Since the cryogenic bearing should be experimented under an extreme condition, namely a cryogenic environment, this allows only a limited access and data may not be easily obtained using electric instruments.

SUMMARY

The present disclosure is directed to providing a test apparatus, which may efficiently measure a single torque of a bearing, which is a main factor of a bearing durability soundness test, and efficiently tests durability of a cryogenic bearing which operates in a cryogenic environment.

In one aspect, there is provided a bearing test apparatus for testing durability of a bearing, which includes: a bearing cap coupled to an outer ring of a bearing to be tested (hereinafter, referred to as a "test bearing"); a driving rotary shaft coupled to an inner ring of the test bearing to rotate the inner ring; and a bearing torque meter for measuring a single torque of the test bearing, wherein an extension bar is formed at the bearing cap to protrude thereon, wherein the bearing torque meter includes a measurement rod configured to contact the extension bar and be fixed to support the extension bar in a direction opposite to a rotating direction of the driving rotary shaft; and a power sensor for measuring a force applied to the measurement rod, and wherein the single torque of the test bearing is calculated based on a distance from the driving rotary shaft to the measurement rod and a force applied to the measurement rod.

According to an embodiment, the bearing test apparatus may further include: a radial rod configured to extend in a radial direction of the driving rotary shaft to apply a radial load to the bearing cap; and an axial rod configured to extend in an axial direction of the driving rotary shaft to apply an axial load to the bearing cap.

According to an embodiment, a wheel capable of rotating based on an axis parallel to the driving rotary shaft may be provided at an end of the radial rod which comes in contact with a side of the bearing cap.

According to an embodiment, the axial rod and the driving rotary shaft may be concentrically arranged, and an end of the axial rod which comes in contact with an upper surface of the bearing cap may be sharp.

According to an embodiment, the bearing test apparatus may include a chamber for partially accommodating the bearing cap, the test bearing and the driving rotary shaft therein, the test bearing may be a cryogenic bearing which operates in a cryogenic environment, and a cryogenic fluid may be injected into the chamber.

According to an embodiment, the test apparatus may further include a rotary shaft housing coupled to the chamber and surrounding the driving rotary shaft which extends out of the chamber, the driving rotary shaft may be rotatably supported to the rotary shaft housing by means of a support bearing, and a sealing member may be formed at a connection unit of the chamber and the rotary shaft housing to isolate the chamber and the rotary shaft housing from each other.

According to an embodiment, the test apparatus may include: a cryogenic fluid injection tube extending from an outside of the chamber into the chamber; and a cryogenic fluid discharge tube extending from an inside of the chamber out of the chamber, wherein the cryogenic fluid injection tube may communicate with the bearing cap.

According to an embodiment, the extension bar may be a hollow pipe communicating with an inside of the bearing cap, and the cryogenic fluid injection tube may be connected to and communicates with the extension bar.

According to an embodiment, at least a part of the cryogenic fluid injection tube in the chamber may be formed with a flexible member.

According to an embodiment, a driving motor for transmitting a rotating force to the driving rotary shaft may be connected to the driving rotary shaft by means of a connection rotary shaft, and the driving rotary shaft and the connection rotary shaft may be connected by means of a flexible coupling, and the connection rotary shaft and the driving motor may be connected by means of a flexible coupling.

According to an embodiment, the test apparatus may include: a vibration sensor for measuring a vibration generated from the test apparatus; or an acoustic sensor for measuring a sound generated from the test apparatus, or both the vibration sensor and the acoustic sensor, wherein the bearing test apparatus may further include a frequency analyzer for analyzing a frequency of a signal measured by the vibration sensor and the acoustic sensor.

According to an embodiment, the frequency analyzer may classify a signal frequency generated according to an operation of the test bearing by removing a signal frequency, which appears when operating the driving rotary shaft in a state where the test bearing is not mounted, from a signal frequency which appears when operating the driving rotary shaft in a state where the test bearing is mounted.

According to an embodiment, when a change rate of torque of the test bearing is a predetermined level or above, the test apparatus may determine that the test bearing is abnormal and generate a warning alarm.

According to an embodiment, the test apparatus may include: a temperature sensor and a pressure sensor for measuring temperature and pressure of an inlet of the cryogenic fluid injection tube and an outlet of the cryogenic fluid discharge tube; and a flow meter for measuring a flow rate of the cryogenic fluid injection tube, wherein a phase change of the cryogenic fluid is checked by using measurement values of the temperature sensor, the pressure sensor and the flow meter.

According to an embodiment, measurement values of the temperature sensor, the pressure sensor and the flow meter may be displayed on a monitor.

DETAILED DESCRIPTION

Figure 1:
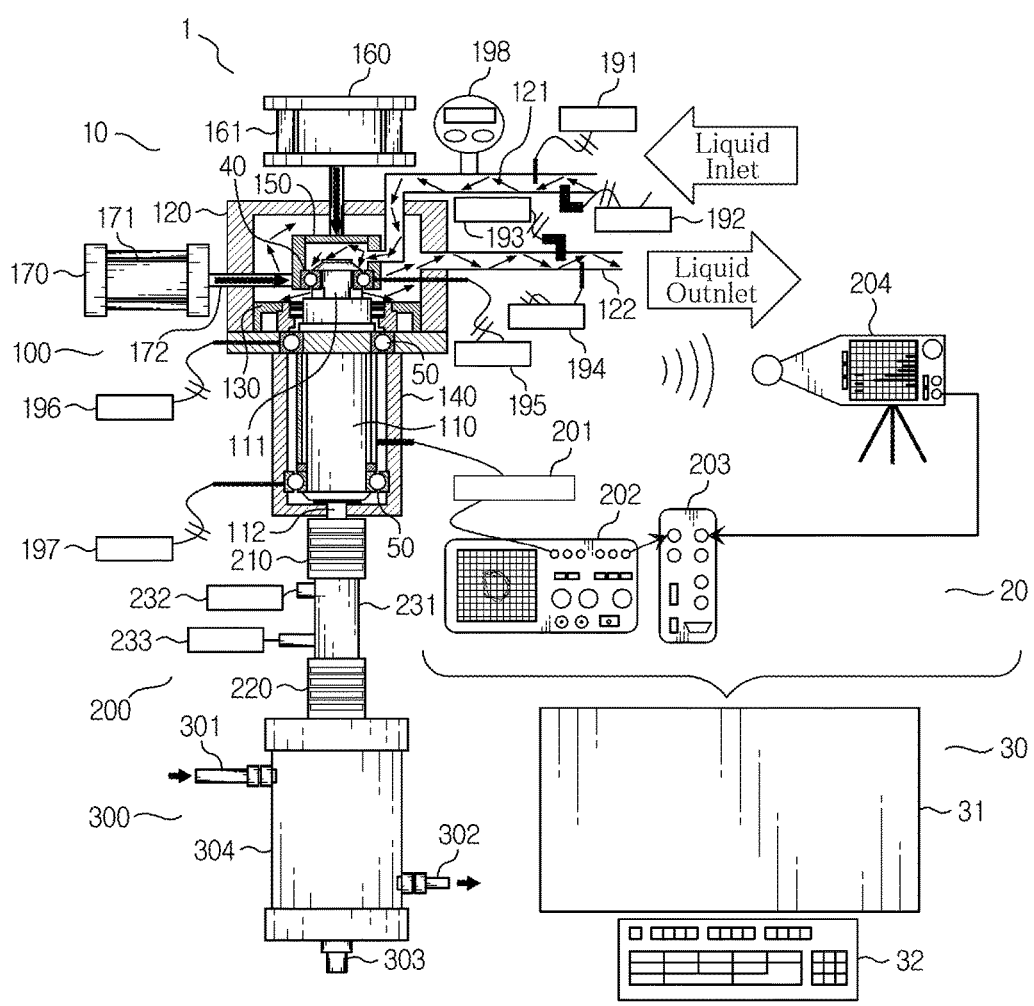
FIG. 1 is a diagram showing a bearing test apparatus according to an embodiment of the present disclosure.

Hereinafter, embodiments of the present disclosure will be described with reference to the accompanying drawings. Even though the present disclosure is described with reference to the embodiments depicted in the drawings, the technical spirit, essence and operation of the present disclosure are not limited thereto.

Figure 2:
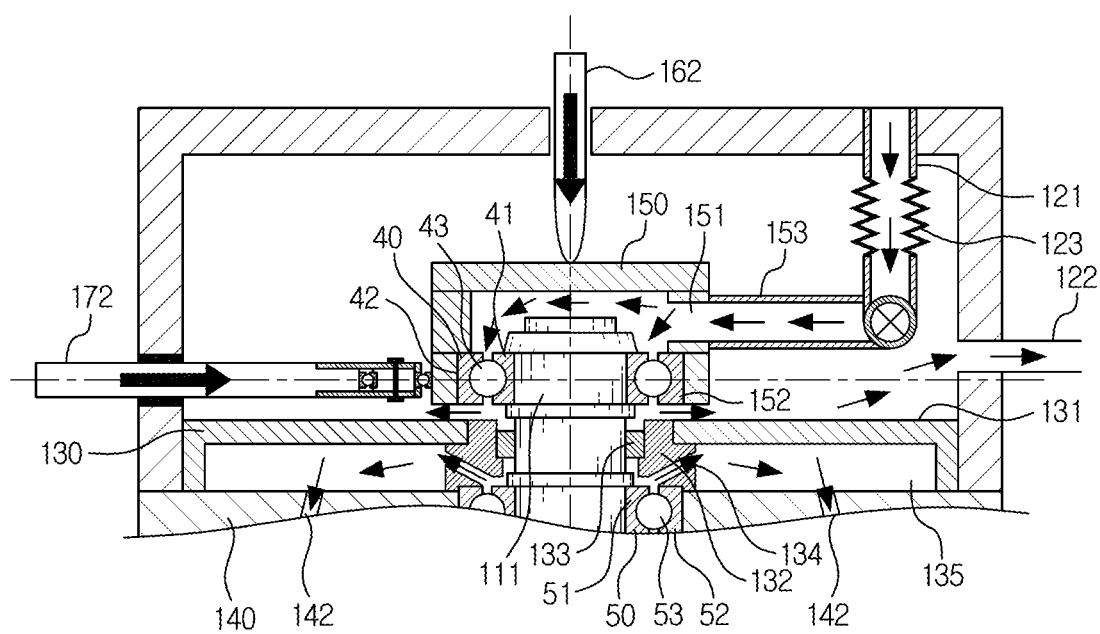
FIG. 2 is a cross-sectional view showing a part of a top portion of the test apparatus of FIG. 1, observed from a side.
Figure 3:
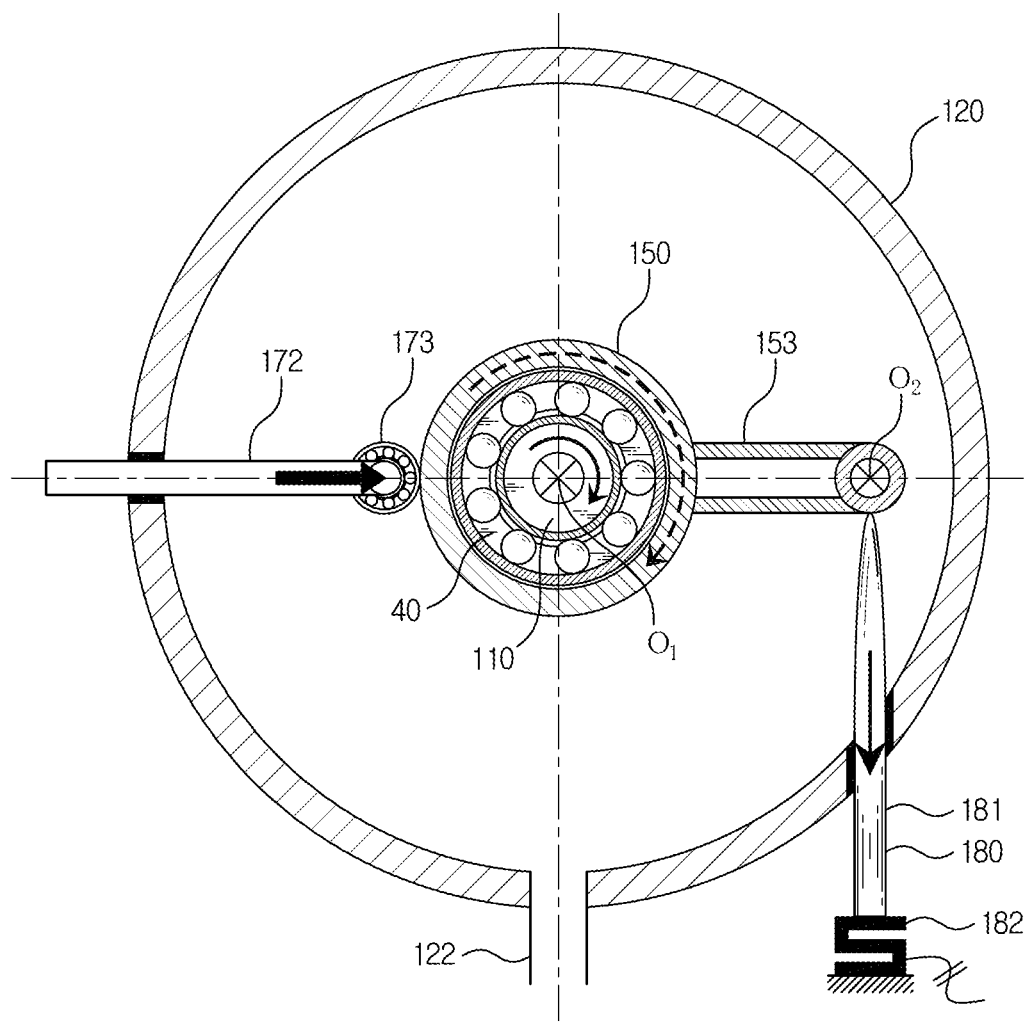
FIG. 3 is a cross-sectional view showing the test apparatus of FIG. 1, observed from the above.

FIG. 1 is a diagram showing a bearing test apparatus according to an embodiment of the present disclosure. FIG. 2 is a cross-sectional view showing a part of a top portion of the test apparatus of FIG. 1, observed from a side, and FIG. 3 is a cross-sectional view showing the test apparatus of FIG. 1, observed from the above.

As shown in FIG. 1, a bearing test apparatus 1 includes a measurement unit 10 for testing a bearing 40 to be tested (hereinafter, referred to as a "test bearing") 40, an analyzing unit 20 for collecting and analyzing various signals measured by the measurement unit 10, and a control unit 30 for controlling the bearing test apparatus 1 and displaying the signals collected and analyzed by the analyzing unit 20.

The measurement unit 10 includes a test unit 100 at which the test bearing 40 is mounted, a driving unit 300 for providing a driving force to rotate a driving rotary shaft 110 connected to the test bearing 40, and a connection unit 200 for connecting the driving unit 300 to the driving rotary shaft 110.

The test unit 100 includes a rotary shaft housing 140 for fixedly supporting the rotary shaft 110 in a vertical direction, and a chamber 120 coupled to the rotary shaft housing 140.

As shown in FIGS. 1 to 3, the chamber 120 accommodates a part of the driving rotary shaft 110, which protrudes above the rotary shaft housing 140, in an inner space thereof.

The test bearing 40 is mounted to one end 111 of the driving rotary shaft 110 located in the chamber 120. The other end 112 of the driving rotary shaft 110 protrudes below the rotary shaft housing 140 and is connected to the connection unit 200.

A bearing cap 150 is coupled to the test bearing 40 to surround the test bearing 40.

The test bearing 40 of this embodiment is a ball bearing including an inner ring 41, an outer ring 42 and a ball 43 between the inner and outer rings. The inner ring 41 of the test bearing 40 is interposed at the end 111 of the driving rotary shaft 110.

The outer ring 42 of the test bearing 40 is detachably coupled to the bearing cap 150. The bearing cap 150 is fixed only to the outer ring 42 of the test bearing 40 so that a load applied to the bearing cap 150 is entirely transmitted to the test bearing 40.

In addition, the test bearing 40 of this embodiment is a cryogenic bearing which operates in a cryogenic environment.

In this embodiment, in order to realize an operation environment of the cryogenic bearing, the test bearing 40 is exposed to a cryogenic fluid in operation. In this embodiment, the cryogenic fluid is for example liquid nitrogen ($LN_2$).

A cryogenic fluid injection tube 121 is formed from an outside of the chamber 120 therein through a through hole formed in an outer wall of the chamber 120, and the cryogenic fluid injection tube 121 communicates with an inside of the bearing cap 150 in the chamber 120.

In detail, as well shown in FIG. 2, an extension bar 153 protrudes on a side of the bearing cap 150.

One end of the extension bar 153 is a hollow pipe communicating with a fluid inlet 151 formed in a side of the bearing cap 150, and the other end of the extension bar 153 is connected to and communicates with the cryogenic fluid injection tube 121 which vertically extends into the chamber 120.

In addition, a cryogenic fluid discharge tube 122 is formed from the inside of the chamber 120 to an outside thereof through a through hole formed in the outer wall of the chamber 120.

A cryogenic fluid is injected through the cryogenic fluid injection tube 121 from the outside and flows into the bearing cap 150, and the cryogenic fluid lubricates and cools the test bearing 40 while passing through the test bearing 40. The cryogenic fluid passes between the inner ring 41 and the outer ring 42 of the test bearing 40 and discharges from the bearing cap 150 through a fluid outlet 152 formed near the bearing cap 150. The cryogenic fluid discharged from the bearing cap 150 stays in the inner space of the chamber 120 and discharges through the cryogenic fluid discharge tube 122.

In this embodiment, in order to prevent the cryogenic fluid flowing in the chamber 120 from giving any influence to components other than the inner configuration of the chamber 120, a sealing member 130 is formed at a connection unit between the chamber 120 and the rotary shaft housing 140 to isolate the chamber 120 from the rotary shaft housing 140.

The sealing member 130 includes a plate 131 serving as a horizontal barrier in the chamber 120, a nut 132 surrounding the driving rotary shaft 110, and a lip seal 133 for sealing a gap between the nut 132 and the driving rotary shaft 110.

The sealing member 130 forms a predetermined gap between the inside of the chamber 120 and the rotary shaft housing 140, so that the cryogenic environment in the chamber 120 is separated from the rotary shaft housing 140.

In the rotary shaft housing 140, the driving rotary shaft 110 is rotatably supported by means of two support bearings 50.

The support bearing 50 is a ball bearing including an inner ring 51, an outer ring 52, and a ball 53 between the inner and outer rings. The inner ring 51 of the support bearing 50 is fit into a body of the driving rotary shaft 110, and the outer ring 52 is coupled to the rotary shaft housing 140.

The inside of the rotary shaft housing 140 is in a normal temperature environment, and the support bearing 50 may be a general bearing which is lubricated by an oil in a normal temperature environment.

This is enabled by isolating the chamber 120 of a cryogenic environment from the rotary shaft housing 140 of a normal temperature environment by means of the sealing member 130 described above.

By separating the bearing installed at the test unit 100 into the cryogenic test bearing 40 and two oil-lubricating support bearings 50, the number of cryogenic bearings consumed at every experiment may be reduced to at least ⅓, different from an existing technique in which both a test bearing and a support bearing employ the cryogenic bearing.

In addition, it is possible to figure out characteristics of a single unit of the test bearing 40. In other words, if the support bearing 50 is not broken, it is possible to exchange only the test bearing 40 mounted at the top portion and use the test bearing for an experiment. Moreover, test bearings 40 of various sizes may be applied to the same system by using a spacer or the like and then a durability test may be performed thereto.

The support bearing 50 is lubricated by the oil supplied into the rotary shaft housing 140.

An oil passage 134 is formed through the nut 132 of the sealing member 130, and an oil outlet 142 is formed through the top surface of the rotary shaft housing 140.

Oil flows into the rotary shaft housing 140 through an oil inlet (not shown) formed in a lower sidewall of the rotary shaft housing 140, and the oil passes through the support bearing 50 to lubricate the support bearing 50. The oil passing through the gap between the inner and outer rings of the support bearing 50 flows through the oil passage 134 and discharges through the oil outlet 142. The oil is supplied through an oil pump (not shown), cooled by a cooler, and then supplied into the rotary shaft housing 140 again.

Meanwhile, one of main factors associated with durability life of the test bearing 40 is a bearing torque which should be endured by the test bearing 40 in operation. In this embodiment, the bearing test apparatus 1 includes a bearing torque meter 180 for directly measuring the torque of the test bearing 40.

Since a cryogenic environment is formed in the chamber 120 by means of a cryogenic fluid, if a torque is measured using an electronic device, costs and efficiency may deteriorate.

Therefore, the bearing torque meter 180 of this embodiment has a mechanical configuration in order to minimize an electronic device exposed to the cryogenic environment.

As shown in FIG. 3, the bearing torque meter 180 includes a measurement rod 181 extending through the chamber 120, and a power sensor 182 connected to an end of the measurement rod 181 exposed out of the chamber 120.

The measurement rod 181 extends in a direction orthogonal to both an axial direction and a radial direction of the driving rotary shaft 110. In other words, the measurement rod 181 is orthogonal to the extension bar 153 which extends in orthogonal to the axial direction of the driving rotary shaft 110 and parallel to the radial direction of the driving rotary shaft 110.

The measurement rod 181 passes the chamber 120 through a through hole formed in an outer wall of the chamber 120. A seal made of flexible material is provided at the through hole of the chamber 120 through which the measurement rod 181 passes, so that the inside of the chamber 120 is sealed and also the measurement rod 181 is not confined by the chamber 120.

An end of the measurement rod 181 comes into contact with an end of the extension bar 153. The measurement rod 181 is fixed to support the extension bar 153 in a direction opposite to a rotating direction (a counterclockwise direction on the figure) of the driving rotary shaft 110.

The power sensor 182 measures a force applied to the measurement rod 181 by the bearing cap 150.

The single torque of the test bearing 40 represents a torque applied to the outer ring 42 by a power transmitted by the rotating force of the inner ring 41 which rotates together with the driving rotary shaft 110.

In this embodiment, since the bearing cap 150 is not confined by the chamber 120 but is coupled to the outer ring 42 of the test bearing 40, the torque of the outer ring 42 means the torque of the bearing cap 150.

Since a distance L from an axial center ($O_1$) of the driving rotary shaft 110 to an end ($O_2$) of the extension bar 153 in contact with the measurement rod 181 is known, the single torque of the test bearing 40 can be calculated by multiplying the distance L by the force (F) measured by the power sensor 181.

The bearing torque meter 180 of this embodiment may not only prevent the measurement efficiency from deteriorating due to a cryogenic environment but also quantitatively evaluate durability soundness of the test bearing 40 by measuring an independent torque of a single unit of the test bearing.

In addition, since the cryogenic fluid provided to the chamber 120 flows into the bearing cap 150 and then discharges out through the test bearing 40, the change of bearing torque according to a flow rate of the cryogenic fluid passing through the inner and outer rings of the test bearing 40 may be effectively sensed.

Meanwhile, a great load may be applied to the test bearing 40 depending on an environment in which the test bearing 40 is used, for example a space launch vehicle.

In this embodiment, in order to reproduce the load applied to the test bearing 40, a device for applying a radial load and/or an axial load to the test bearing 40 is provided.

As shown in FIG. 1, the axial load generating device 160 includes an axial rod 162 extending in an axial direction of the driving rotary shaft 110, and a hydraulic cylinder 161 for moving the axial rod 162 forwards or rearwards in the axial direction of the driving rotary shaft 110.

The radial load generating device 170 includes a radial rod 172 extending in a radial direction of the driving rotary shaft 110, and a hydraulic cylinder 171 for moving the radial rod 172 forwards or rearwards in the axial direction of the driving rotary shaft 110.

The axial rod 162 and the radial rod 172 pass through the chamber 120 through the through hole formed in the outer wall of the chamber 120.

A seal made of flexible material is provided at the through hole of the chamber 120 through which the axial rod 162 and the radial rod 172 pass, so that the inside of the chamber 120 is sealed and also the axial rod 162 and the radial rod 172 are not confined by the chamber 120.

The axial rod 162 and the radial rod 172 push the bearing cap 150 to give a load thereto, thereby reproducing an axial load and a radial load applied to the test bearing 40, respectively.

Referring to FIGS. 2 and 3, an end of the axial rod 162 which comes in contact with an upper surface of the bearing cap 150 is sharp, and the axial rod 162 is concentrically arranged with the driving rotary shaft 110 since a central axis of driving rotary shaft 110 is identical to a central axis of the driving rotary shaft 110. Therefore, the degree of freedom of the bearing cap 150 receiving a force by the test bearing 40 is not influenced by the axial rod 162.

A wheel capable of rotating based on an axis parallel to the driving rotary shaft 110 is provided at an end of the radial rod 172 which comes in contact with a side of the bearing cap 150. In this embodiment, the wheel 173 is formed with a ball bearing.

Since the wheel 173 may roll with respect to a side of the bearing cap 150, the degree of freedom of the bearing cap 150 is not influenced by the radial rod 172.

As best shown in FIG. 2, at least a part of the cryogenic fluid injection tube 121 extending into the chamber 120 is formed with a flexible tube 123, so that the cryogenic fluid injection tube 121 may be freely bent.

Therefore, even though a load is applied to the bearing cap 150 by the axial rod and/or the radial rod, the degree of freedom of the entire bearing cap 150 connected to the chamber 120 by means of the extension bar 153 and the cryogenic fluid injection tube 121 is not confined by the chamber 120.

Referring to FIG. 1 again, the driving unit 300 may include a driving motor 304, which is an induced motor, and adjust RPM and acceleration/deceleration by means of an inverter. The driving motor 304 is cooled by a coolant which flows from a coolant inlet 301 to a coolant outlet 302.

The driving unit 300 and the measurement unit 100 are connected to each other by means of a connection unit 200.

The connection unit 200 includes a connection rotary shaft 231 arranged in a line with the driving rotary shaft 110 and the motor rotary shaft 303 of the driving motor 304.

The connection rotary shaft 231 of the connection unit 200 and the driving rotary shaft 110 as well as the connection rotary shaft 231 and the motor rotary shaft 303 are connected to each other flexible couplings 210, 220 of flexible material.

The flexible couplings 210, 220 allow a center of each rotary shaft to be slightly dislocated, thereby minimizing inferior arrangement thereof.

If the motor rotary shaft 303 of the driving motor rotates, the connection rotary shaft 231 of the connection unit 200 rotates by means of the flexible coupling 220, and the rotating force of the connection rotary shaft 231 is transmitted to the driving rotary shaft 110 by means of the flexible coupling 210 to rotate the driving rotary shaft 110.

As shown in FIG. 1, in this embodiment, a thermocouple is inserted into the cryogenic fluid inlet tube 121 and the cryogenic fluid discharge tube 122 to form temperature sensors 191, 194 for measuring a temperature of the cryogenic fluid in the tubes. In addition, pressure sensors 192, 193 for measuring a pressure in the tubes are formed in the cryogenic fluid inlet tube 121 and the cryogenic fluid discharge tube 122. In addition, a flow meter 198 for checking a flow rate of the cryogenic fluid is provided at the cryogenic fluid inlet tube 121.

By using measurement values of the temperature sensors 191, 194, the pressure sensors 192, 193 and the flow meter 198, it is possible to check conditions of the inlet and the outlet of the test unit 100 and actual boundary conditions of a phase change (gas, liquid) of the cryogenic fluid.

A small hole is processed in the bearing cap 150 at a portion which comes into contact with the outer circumference of the outer ring 42 of test bearing 40, and a thermocouple is inserted therein to form a temperature sensor 195 for measuring a temperature of the test bearing 40. An amount of heat generated by the test bearing 40 may be evaluated using the temperature sensor 195.

Temperature sensors 196, 197 may also be formed at two support bearings 50 lubricated by oil to check temperatures of both support bearings 50. Since the thermocouples of the temperature sensors 196, 197 directly come into contact with the outer ring 52 of the support bearing 50 and measure a temperature of the outer ring 52 of the support bearing 50, the operation stability of the support bearing may be checked.

The connection unit 200 includes a RPM meter 233 for measuring an RPM of a rotating system and a torque meter 232 for measuring a torque.

By measuring a torque of the entire top portion of the torque meter 232 other than the rotating system and the driving unit 300, it is possible to perform an experiment while directly monitoring stability of the entire test environment (the support bearing and the test bearing).

Meanwhile, the test apparatus 1 of this embodiment includes a vibration sensor 201 for measuring a vibration generated from the test apparatus 1. The vibration sensor 201 is configured with a displacement sensor disposed between the rotary shaft housing 100 and the support bearing 50.

In addition, the test apparatus 1 may include an acoustic sensor 204 for measuring a sound generated from the test apparatus 1.

The analyzing unit 20 includes a frequency analyzer (FFT analyzer) 203 for analyzing a frequency of the signal measured by the vibration sensor 201 and the acoustic sensor 204. The vibration measured by the vibration sensor 201 is signalized by means of an oscilloscope 202.

The frequency analyzer 203 converts the vibration and sound signals into spectrum and analyzes the same. When the signal frequency measured by the vibration sensor 201 and the acoustic sensor 204 is converted into spectrum and analyzed, a signal generated by each component of the test apparatus 1 may be classified into an inherent frequency band of the corresponding component.

In order to evaluate durability of the test bearing 40, it is needed to classify an inherent signal frequency of the test bearing 40, which is generated by the operation of the test bearing.

In this embodiment, first, vibration and/or sound signal frequency (hereinafter, referred to as an "initial signal frequency") measured from the test apparatus 1 when the driving rotary shaft 110 is operated in a state where the test bearing 40 is not mounted is collected. Next, vibration and/or sound signal frequency (hereinafter "test signal frequency") measured from the test apparatus 1 when the driving rotary shaft 110 is operated in a state where the test bearing 40 is mounted is collected.

The frequency analyzer 203 extracts the inherent signal frequency of the test bearing 40 by removing an initial signal frequency from the test signal frequency.

If analyzing the inherent signal frequency of the test bearing 40, it is possible to quantitatively evaluate whether the test bearing 40 is broken, and accordingly it is possible to determine the durability soundness of the test bearing 40.

Meanwhile, all signals observed by the bearing torque meter 180 and various sensors such as a temperature sensor and a pressure sensor of the test apparatus 1 are transmitted to the control unit 30.

The control unit 30 is a computer system including a monitor panel 31 and a keyboard 32.

Figure 4:
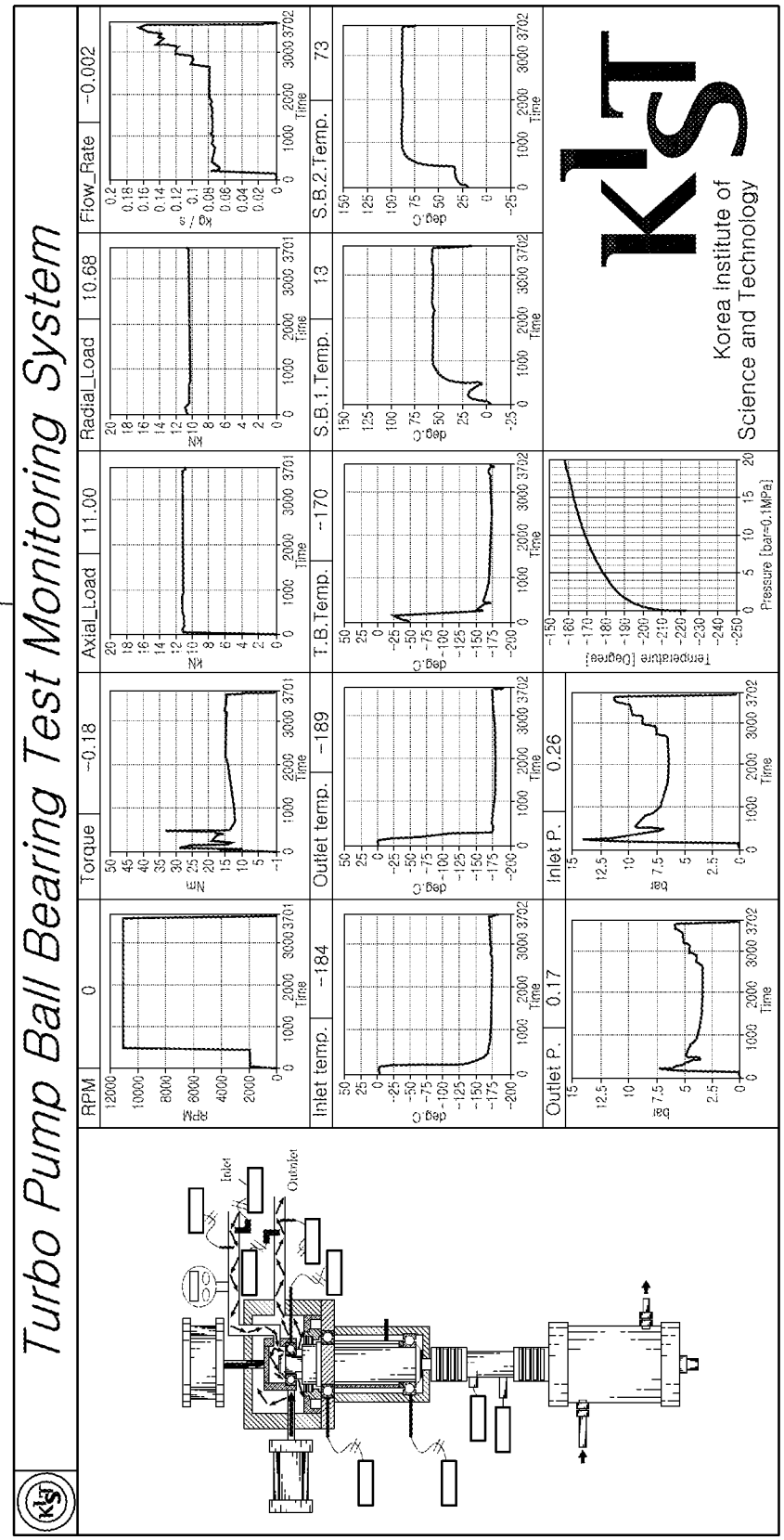
FIG. 4 is a diagram showing an example of data about the test apparatus, displayed on a monitor panel.

FIG. 4 is a diagram showing an example of data about the test apparatus 1, displayed on a monitor panel.

A user may check and evaluate all data through the monitor 31 by reading voltage signals of all meters and sensors of the test apparatus 1.

In the test apparatus 1 of this embodiment, if a change rate of torque of the test bearing 40 changes over 10% from a stabilized torque after operation, it is determined that the test bearing 40 is abnormal, and generates a warning alarm so that the test is intercepted.

If the change rate of torque is abnormal, it is possible to quantitatively evaluate a minute damage of the test bearing 40 by analyzing vibration and sound signals.

The bearing test apparatus 1 of this embodiment may adjust a radial load and an axial load of the test bearing by using a hydraulic cylinder, and the test unit 100 is classified into a support bearing and a test bearing which allows characteristics of a single unit of the test bearing 40 to be efficiently tested.

In addition, since the test bearing and the support bearing are isolated from each other, the present disclosure may be efficiently used to a durability of a special bearing operating in a special environment, for example a cryogenic environment or a space launch vehicle.

What is claimed is:

1. A bearing test apparatus comprising:
   a bearing cap coupled to an outer ring of a test bearing;
   a hollow extension bar configured to transport cryogenic fluid to an inside of the bearing cap;
   a driving rotary shaft coupled to an inner ring of the test bearing to rotate the inner ring; and
   a bearing torque meter configured to measure a torque of the test bearing, and comprising:
      a measurement rod configured to contact the extension bar and be fixed to support the extension bar in a direction opposite to a rotating direction of the driving rotary shaft; and
      a power sensor configured to measure a force applied to the measurement rod, and
   wherein the torque of the test bearing is determined based on a distance from the driving rotary shaft to the measurement rod and a force applied to the measurement rod.

2. The bearing test apparatus according to claim 1, further comprising:
   a radial rod configured to extend in a radial direction of the driving rotary shaft to apply a radial load to the bearing cap; and
   an axial rod configured to extend in an axial direction of the driving rotary shaft to apply an axial load to the bearing cap.

3. The bearing test apparatus according to claim 2, wherein a wheel capable of rotating based on an axis parallel to the driving rotary shaft is provided at an end of the radial rod which comes in contact with a side of the bearing cap.

4. The bearing test apparatus according to claim 2, wherein the axial rod and the driving rotary shaft are concentrically arranged, and
   wherein an end of the axial rod which comes in contact with an upper surface of the bearing cap.

5. The bearing test apparatus according to claim 1, wherein the bearing test apparatus comprises a chamber partially accommodating the bearing cap, the test bearing, and the driving rotary shaft therein, and
   wherein the cryogenic fluid is injected into the chamber.

6. The bearing test apparatus according to claim 5, further comprising:
   a rotary shaft housing coupled to the chamber and surrounding the driving rotary shaft which extends out of the chamber,
   wherein the driving rotary shaft is rotatably supported to the rotary shaft housing by means of a support bearing, and
   wherein a sealing member is formed at a connection unit of the chamber and the rotary shaft housing to isolate the chamber and the rotary shaft housing from each other.

7. The bearing test apparatus according to claim 5, further comprising:
   a cryogenic fluid injection tube extending from an outside of the chamber into the chamber; and
   a cryogenic fluid discharge tube extending from an inside of the chamber out of the chamber,
   wherein the cryogenic fluid injection tube communicates with the bearing cap.

8. The bearing test apparatus according to claim 7, wherein the extension bar is a hollow pipe communicating with an inside of the bearing cap, and
   wherein the cryogenic fluid injection tube is connected to and communicates with the extension bar.

9. The bearing test apparatus according to claim 8, wherein at least a part of the cryogenic fluid injection tube in the chamber is formed with a flexible member.

10. The bearing test apparatus according to claim 1, wherein a driving motor configured to transmit a rotating force to the driving rotary shaft is connected to the driving rotary shaft by means of a connection rotary shaft, and
    wherein the driving rotary shaft and the connection rotary shaft are connected by means of a flexible coupling, and the connection rotary shaft and the driving motor are connected by means of a flexible coupling.

11. The bearing test apparatus according to claim 1, comprising:
    a vibration sensor configured to measure a vibration generated from the test apparatus; or
    an acoustic sensor configured to measure a sound generated from the test apparatus; or
    both the vibration sensor and the acoustic sensor,
    wherein the bearing test apparatus further comprises a frequency analyzer configured to analyze a frequency of a signal measured by the vibration sensor and the acoustic sensor.

12. The bearing test apparatus according to claim 11, wherein the frequency analyzer is configured to classify a signal frequency generated according to an operation of the test bearing by removing a signal frequency, which appears when operating the driving rotary shaft in a state where the test bearing is not mounted, from a signal frequency which appears when operating the driving rotary shaft in a state where the test bearing is mounted.

13. The bearing test apparatus according to claim 1,

Wherein, in response to a change rate of torque of the test bearing being a predetermined level or above, it is determined that the test bearing is abnormal and a warning alarm is generated.

14. The bearing test apparatus according to claim 7, further comprising:
- a temperature sensor and a pressure sensor configured to measure temperature and pressure, respectively, of an inlet of the cryogenic fluid injection tube and an outlet of the cryogenic fluid discharge tube; and
- a flow meter configured to measure a flow rate of the cryogenic fluid injection tube,
- wherein a phase change of the cryogenic fluid is checked by using measurement values of the temperature sensor, the pressure sensor and the flow meter.

15. The bearing test apparatus according to claim 14,
wherein measurement values of the temperature sensor, the pressure sensor, and the flow meter are displayed on a monitor.

* * * * *